(12) United States Patent
Seidel

(10) Patent No.: US 11,311,499 B2
(45) Date of Patent: Apr. 26, 2022

(54) CANNABINOID FORMULATION CONTAINING ACTIVE INGREDIENTS AND CARRIER FOR TRANSDERMAL ABSORPTION TO TREAT NEUROPATHY

(71) Applicant: Diesel-Stilfen, LLC, South Portland, ME (US)

(72) Inventor: William Seidel, Lady Lake, FL (US)

(73) Assignee: William Seidel, Lady Lake, FL (US)

( * ) Notice: Subject to any disclaimer, the term of this patent is extended or adjusted under 35 U.S.C. 154(b) by 143 days.

(21) Appl. No.: 16/931,763

(22) Filed: Jul. 17, 2020

(65) Prior Publication Data

US 2022/0016047 A1    Jan. 20, 2022

(51) Int. Cl.
| | | |
|---|---|---|
| *A61K 36/00* | (2006.01) | |
| *A61K 31/05* | (2006.01) | |
| *A61K 9/06* | (2006.01) | |
| *A61K 36/73* | (2006.01) | |
| *A61K 47/44* | (2017.01) | |
| *A61K 47/46* | (2006.01) | |
| *A61K 9/00* | (2006.01) | |
| *A61K 31/12* | (2006.01) | |

(52) U.S. Cl.
CPC ............ *A61K 31/05* (2013.01); *A61K 9/0014* (2013.01); *A61K 9/06* (2013.01); *A61K 31/12* (2013.01); *A61K 36/73* (2013.01); *A61K 47/44* (2013.01); *A61K 47/46* (2013.01); *A61K 2236/15* (2013.01); *A61K 2236/17* (2013.01); *A61K 2236/333* (2013.01); *A61K 2236/51* (2013.01); *A61K 2236/53* (2013.01)

(58) Field of Classification Search
None
See application file for complete search history.

(56) References Cited

U.S. PATENT DOCUMENTS

2020/0245666 A1\* 8/2020 Spall .................... A23L 33/105

\* cited by examiner

*Primary Examiner* — Michael V Meller
(74) *Attorney, Agent, or Firm* — Stanton IP Law Firm, P.A.

(57) ABSTRACT

The invention relates to a topical formulation in order to deliver an effective amount of broad-spectrum cannabidiol ointment, in conjunction with active ingredients, menthol and camphor. This invention is for the treatment of symptoms and improvement of sensation associated with peripheral neuropathy, particularly of the feet and hands. The present invention also provides for various topical application formulations.

1 Claim, 3 Drawing Sheets

CANNABINOID FORMULATION CONTAINING ACTIVE INGREDIENTS AND CARRIER FOR TRANSDERMAL ABSORPTION TO TREAT NEUROPATHY

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

Trademarks used in the disclosure of the invention and the applicants make no claim to any trademarks referenced.

BACKGROUND OF THE INVENTION

1) Field of the Invention

The invention relates to compositions and methods for relieving neuropathy using formulations of cannabidiol enhanced to promote transdermal absorption. And more particularly, to a cream or ointment that can be applied to the skin to relieve neuropathy.

2) Description of Related Art

A common cause of peripheral neuropathy is diabetes, but it can also result from injuries, infections, exposure to toxins, high blood pressure, obesity, chemotherapy treatment, and heavy alcohol use. Idiopathic peripheral neuropathy is when the conditions' cause is unable to be determined. Additionally, persons in certain professions requiring repetitive motions may suffer nerve compression resulting in symptoms.

Symptoms include pain, a pins-and-needles sensation, numbness, and weakness. The damage is caused by lack of blood flow to the nerves in the hands and feet thus causing the nerves to become diseased, due to the lack of nutrients and oxygen. Nerves require a continuous supply of oxygen to function properly.

Commonly cited statistics for neuropathy include 60% to 70% of people with diabetes, 30% to 40% of people who receive chemotherapy to treat cancer, and 30% of people who have human immunodeficiency virus (HIV).

Current therapies include prescription medications such as antidepressants like amitriptyline, pain medications like oxycodone, anti-seizure medications, and pain-relieving creams, and are used to lessen symptoms; OTC pharmaceuticals (analgesics, creams); and nutritional supplementation (B vitamin complex, alpha lipoic acid, acetyl L-carnitine). Research has shown that maintaining a gluten-free diet reduces symptoms even with persons that have no allergy to gluten.

The American Pain Society recommends that pain be made more visible and categorized as the fifth vital sign.

Physicians are often reluctant to administer large doses of analgesic drugs for fear of respiratory depression or other complications. The same holds true for currently available opioid-based drug therapies which can produce undesirable side effects such as hallucinations, constipation, sedation, nausea and dysphoria.

Therefore, pain management due to peripheral neuropathy is a great challenge for health care professionals, as pain often can debilitate individuals in ways that affect their day-to-day functioning and productivity.

Health economists writing in The Journal of Pain in September 2012, reported that the annual estimated national cost of pain management ranges from $560 billion to $635 billion.

Doctors and pain management physicians all agree that topical pain management is preferable to the administration of antidepressants like amitriptyline, pain medications like oxycodone, and anti-seizure medications to treat the associated pain of peripheral neuropathy.

Numerous articles in the relevant literature have reported the use of cannabis to treat pain to treat peripheral neuropathy: 1. Stander, S., M., Schmelz, D. Metze, T. Luger, and R. Rukwied. "Distribution of cannabinoid receptor 1 (CB1) and 2 (CB2) on sensory nerve fibers and adnexal structures in human skin" Journal of Dermatological Science 38.3 (2005): 177-188 2. Manzanares, J., M. Julian and A. Carrascosa. "Role of the Cannabinoid System in Pain Control and Therapeutic Implications for the Management of Acute and Chronic Pain Episodes" Current Neuropharmocology. 4.3 (2006): 239-257 3. Jorge, L. L., C. C. Feres and V. E. Teles. "Topical preparations for pain relief: efficacy and patient adherence" Journal of Pain Research. 4 (2011): 11-24. 4. Wantanabe, T., R. Kaji, N. Oka, W. Bara and J. Kimura. All prior art focuses on the use of cannabis to treat the pain however, the use of cannabis is prohibited by Federal law. The contents of the aforementioned articles are incorporated by reference in their entirety.

A review of the related technologies has identified that Cannabidiol (CBD) and cannabinoids extracted from hemp plants (*Cannabis sativa, Cannabis Indica, Cannabis ruderalis*) helps relax the vascular walls of the circulatory system. CBD has also been shown to relax muscles, reduce spasticity, rigidity, and tension as a result of stress or overwork.

Specifically, Cannabidiol is a chemical in the *Cannabis sativa* plant, also known as marijuana or hemp. There are over 80 chemicals, known as cannabinoids, that have been identified in the *Cannabis sativa* plant. Cannabidiol seems to reduce pain and anxiety.

There are well known prior transdermal delivery systems that utilize alcohol, solvents, glycols, heat, and DMSO (dimethylsulfoxide). Some of these systems may also irritate, dehydrate, damage the skin, as well as potentially exhibit various toxic side effects internally.

Menthol and camphor are approved active ingredients in certain over-the-counter topical medications at maximum levels of 16% and 11% by total weight of the mixture respectively. These active ingredients are indicated for the temporary relief of arthritis, joint and muscle pains, strains and simple backache. In addition to these ingredients having therapeutic effects, they have been shown to aid in the absorption of other ingredients, and also increase blood circulation in the application area. Camphor and menthol have been shown to unclog pores which are an entryway to the dermis.

Additionally, oil-based carrier ingredients are used to impart texture for ointments (oil based), creams (oil and water based). Generally, ointments are poor at being absorbed by the skin, however they are easy for the patient to apply and therefore they promote the patient use of the product. Additionally, petrolatum and paraffin are common petroleum-based ingredients used for pharmaceuticals and cosmetics, which also provide texture for ointments. These ingredients have minimal absorption into the skin and are not suitable for use as a carrier system for other ingredients that are targeted by the ointment for absorption. In the case of CBD, a hydrophobic compound that is minimally miscible with water, a cream would not be an effective carrier either. A mix of oil soluble compounds, with high absorption rates would be optimal as a carrier to deliver transdermal medication.

A problem with all ointments, creams, and gels is providing a mechanism which allows the active ingredients of the ointment, cream, or gel to pass through the stratum corneum, epidermis and dermal layer, and enter the superficial vascular plexus for transmission with the body fluids to the nerves, so the active ingredients can treat the source of the pain.

Additionally, physicians are more inclined to prescribe topical solutions rather than pain medications, like oxycodone, to treat peripheral neuropathy, which underscores the need for a non-cannabis Cannabidiol topical solution for peripheral neuropathy.

Therefore, what is needed in the art is a Cannabidiol based topical treatment for peripheral neuropathy.

BRIEF SUMMARY OF THE INVENTION

The invention in one form is directed to a method to create a topical transdermal pharmaceutical delivery system, for the delivery of cannabidiol (CBD) for the treatment of peripheral neuropathy.

The invention in another form provides for a carrier for delivering the active ingredient or ingredients into the epidermis. The carrier is optimized to transport one or more active ingredients across the dermal layer.

In yet another form, the invention has one or more carrier ingredients of the topical transdermal pharmaceutical delivery system, which are selected to ensure the active components remain miscible and absorbable, and that one or more active ingredients aid in preparing the epidermis for optimal absorption of ingredients.

BRIEF DESCRIPTION OF THE DRAWINGS

A further understanding of the nature and advantages of particular embodiments, may be realized by reference to the remaining portions of the specification and the drawings, in which like reference numerals are used to refer to similar components. When reference is made to a reference numeral without specification to an existing sub-label, it is intended to refer to all such multiple similar components.

Corresponding reference characters indicate corresponding parts throughout the several views. The exemplifications setout herein, illustrate embodiments of the invention, and such exemplifications are not to be construed as limiting the scope of the invention in any manner.

DETAILED DESCRIPTION

Figure 1:
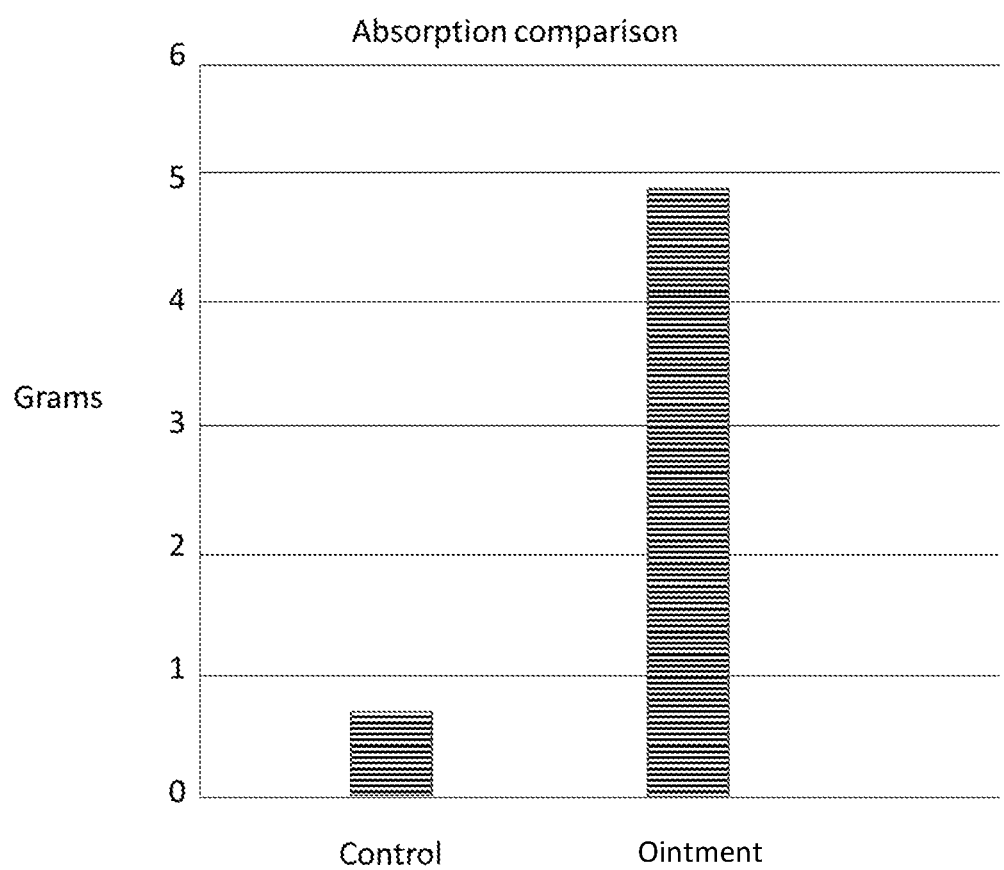
FIG. 1 shows a graph of the absorption comparison utilizing pigs' ears as the test substrate.

In the following description, numerous specific details are set forth. However, it is understood that embodiments of the invention may be practiced without these specific details. In other instances, well-known structures and techniques have not been shown in detail in order not to obscure the understanding of this description. Those of ordinary skill in the art, with the included descriptions, will be able to implement appropriate functionality without undue experimentation.

References in the specification to "one embodiment" or "an embodiment," may indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that such feature, structure, or characteristic may be deployed in connection with other embodiments whether or not explicitly described.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

As this invention is susceptible to embodiments of many different forms, it is intended that the present disclosure be considered as an example of the principles of the invention and not intended to limit the invention to the specific embodiments shown and described.

The terms people, patient, client, user, consumer and individual are used interchangeably to mean an individual who uses the invention.

The term cream, ointment, gel and topical delivery system are used interchangeably to mean an ointment of the invention.

The term tetrahydrocannabinol and THC are used interchangeably in the disclosure and mean tetrahydrocannabinol.

The term Cannabidiol refers to over 80 chemicals, known as cannabinoids, that have been identified in the *Cannabis sativa* plant.

The prior art does not provide for the topical transdermal pharmaceutical delivery system for the delivery of cannabidiol (CBD) for the treatment of peripheral neuropathy. The prior art includes U.S. Pat. No. 10,117,891, Issue Date: Nov. 6, 2018; U.S. Pat. No. 10,450,302, Issue Date: Oct. 22, 2019; U.S. Pat. No. 10,632,064, Issue Date: Apr. 28, 2020, the contents of which are incorporated by reference in their entirety.

In an effort to expand treatment options for persons experiencing peripheral neuropathy, and to reduce costs and minimize time associated with current treatments, a new topical ointment formulation is needed. The instant invention provides a formulation which is suited for the topical treatment of peripheral neuropathy. The formulation includes treatment for, and is not limited to: osteoarthritis, muscle or tendon strains, joint pain, inflammation, lupus and fibromyalgia.

The instant invention achieves the treatment of peripheral neuropathy through the combination of four major components in order to create an optimal topical transdermal pharmaceutical delivery system.

The first component of the formulation is the incorporation of a carrier for delivering the active ingredient or ingredients into the epidermis.

The second component of the formulation is the incorporation of one or more active ingredients designed to treat the condition or conditions.

The third component of the formulation is the incorporation of one or more carrier ingredients to ensure the active components remain miscible and absorbable.

The fourth component of the formulation is the incorporation of one or more active ingredients to aid in preparing the epidermis for optimal absorption of ingredients.

In addition, a fifth component of the formulation, is the incorporation of one or more phytonutrients. Specifically, phytonutrients selected from the group of phytonutrients bearing plants comprising of Glycyrrizaglabra, *Piper longum, Picrorhiza kurroa, Phyllanthus amarus, Bauhinia variegate*, and *Terminalia chebula*. Phytonutrients are natural compounds found in plant foods such as vegetables, fruits, whole grain products and legumes. These plant compounds have beneficial effects working with other essential nutrients to promote good health. The phytonutrients can be incorporated into the formulation, such that they comprise of 1-10 percent of the phytonutrients by weight of the overall formulation.

Of the three active ingredients, the primary active ingredient of the instant invention is cannabidiol (CBD). The preferred form is as a high percentage CBD distillate (85-95% CBD), which also contains other components distilled from the plant, which includes but is not limited to secondary components such as terpenes, flavonoids, other cannabinoids and compounds. The cannabidiol along with these secondary components, contribute to what is termed the entourage effect. The entourage effect is a mechanism by which cannabis compounds other than tetrahydrocannabinol act synergistically to modulate the overall psychoactive effects of the cannabidiol distillate. The process used to produce the high cannabidiol content wax distillate, contains zero or undetectable levels of the psychoactive component Delta-9 THC. Based on the particular cannabidiol percentage level in a sample of wax distillate, the formulation would need to be adjusted to achieve the determined amount of cannabidiol in the finished ointment.

Specifically, when referring to a "Broad-Spectrum" cannabidiol distillate, it is the material processed from the whole plant, and the Delta-9 THC component has been removed Conversely, "Full-Spectrum" cannabidiol (CBD) is processed from the whole plant, and it contains the psychoactive component Delta-9 THC.

Next "CBD Isolate" contains only cannabidiol, without the additional whole leaf components (no other cannabinoids, terpenes, flavonoids, or compounds).

The term "Hemp Oil" generally means "hemp seed oil" which contains little or no CBD.

The term CBD refers to golden colored Cannabidiol oil or cannabidiol. Cannabidiol (CBD) is a phytocannabinoid. It is one of 113 identified cannabinoids in cannabis plants and accounts for up to 40% of the plant's extract.

The term cannabidiol acid (CBD-A), is a dihydroxybenzoic acid that is olivetolic acid in which the hydrogen at position 3 is substituted by a 3-p-mentha-1,8-dien-3-yl (limonene) group. It is a phytocannabinoid, a member of resorcinols, a polyketide and a dihydroxybenzoic acid. It derives from an olivetolic acid. It is a conjugate acid of a cannabidiolate.

The Broad-Spectrum cannabidiol distillate used in this invention is produced through an ethanol extraction process that also employs heat treatment. The whole plant is used (leaves, stems, seeds). The cannabidiol is produced by a vertically integrated manufacturer, to control the life cycle process and limit the introduction of any harmful chemicals. The plants are grown on farms, harvested, homogenized into thermally treated hemp biomass, which is the dried plant matter. The biomass is then distilled using ethanol, which is done to eliminate the THC portion of the extract. This results in an extracted final product which is THC free. The FDA regards ethanol extraction as safe pursuant to FDA guidelines. The distillate is tested analytically, using an independent laboratory, using High-performance liquid chromatography (HPLC) and Gas chromatography (GC) which are approved methodologies for cannabidiol content, Delta-9 THC content, and cannabinoid content.

The production process for the broad-spectrum cannabidiol can be summarized as follows:

1) Plants are harvested and dried to approximately 5% moisture and milled to form a hemp biomass. The milling process breaks the dried cannabis plant into small pieces of a uniform size, ready for the extraction process.
2) Visual inspection, to remove very large stems and any foreign material from the milled hemp biomass.
3) Hemp biomass is cryogenically (−40 C/F) frozen to prevent any moisture uptake and minimize chlorophyll "greening".
4) Then take the hemp biomass and add 1:1 ethanol (200 proof) and hemp biomass by weight, and agitated in a chilled jacketed kettle.
5) Strain and centrifuge the hemp biomass.
6) Then the resulting hemp biomass is boiled under a high vacuum at 19 C/66 F to remove any remaining ethanol.
7) The material from step 6 is winterized (−40 C/F) for 24-36 hours and vacuumed through a Buchner funnel apparatus, which removes wax from the winterized dried material. The Buchner funnel apparatus comprises of a Buchner funnel, which has a piece of qualitative filter paper placed on the perforated floor of the funnel, which then has the winterized dried material placed on the filter paper; a Buchner flask, where the filtrate collects; and the Buchner flask is connected to a vacuum source to create a partial vacuum in the Buchner flask which draws the filtrate into the flask. More specifically, a Buchner Funnel is a fritted/perforated funnel used in commercial laboratories for the vacuum-assisted filtration and separation of liquid substances. Buchner Funnels allow you to filter liquids by pulling them through qualitative filter paper and perforations in the floor or top of the funnel using a vacuum pump.
8) The next step is the decarboxylation step, which is a chemical reaction that removes a carboxyl group and releases carbon dioxide ($CO_2$). The material from step 7 is placed in an oil bath (121 C/250 F), stripping cannabidiol acid (CBD-A), an acid molecule forming a decarboxylation biomass.
9) Then taking the material from Step 8, you apply a High vacuum, which is preferably less than or equal to 1 mmHg (millimeters of Mercury). This separates the tar-like residual plant material from the golden colored cannabidiol distillate which is a Cannabidiol, Broad-Spectrum Cannabidiol oil (CBD). The resulting golden colored cannabidiol distillate is used in the manufacture of the ointment.
10) Taking the ointment and placing it in a suitable container such as a beaker, jar or tube.

The ointment can be used to treat neuropathy by applying it to the skin.

Additional active ingredients are secondary active ingredients and can be selected from menthol and/or camphor. These secondary active ingredients are currently listed in the drug monographs as safe and effective for treating symptoms of pain associated with arthritis, muscle, joints and simple backache. The current invention utilizes these additional actives as an effective adjunct to treat neuropathy. Through use with the cannabidiol (CBD), and the menthol and camphor's propensity to aid in unclogging pores and pore dilation, the three active ingredients may better be absorbed by the carrier.

Carrier for optimal absorption. The carrier is an anhydrous blend of a non-comedogenic native oil soluble with cannabidiol; a non-comedogenic natural wax for product plasticity and absorptive qualities that is not petroleum based; a low molecular weight fatty acid ester or alcohol ester, that exhibits rapid and high absorption and miscible with the other ingredients.

A suitable alcohol ester is Isopropyl myristate, which is the ester of isopropyl alcohol and myristic acid.

Typical non-comedogenic native oil soluble with cannabidiol include olive oil, sun flower seed oil, almond oil. avocado seed oil. cocoa butter. coconut oil. corn oil. cottonseed oil. flax seed oil and grapeseed oil.

Typical non-comedogenic natural wax include bees wax, candelilla wax, carnauba wax, castor wax, ozokerite wax, PEG-8 Bees wax and sunflower wax.

The formulation of the instant invention is assembled from the following materials: Olive oil (CAS No. 8001-25-0), Menthol (CAS No. 89-78-1), Camphor (CAS No. 76-22-2), Isopropyl myristate (CAS No. 110-27-0), Beeswax (CAS No. 8012-89-3), Cannabidiol, Broad-Spectrum Cannabidiol.

When sourcing the Olive oil, (CAS No. 8001-25-0) care is required to ensure that the compound used is refined (*Olea europaea* L.), including blended, virgin and pomace. Olive oil is low (2) on the (0 to 5) comedogenic scale (pore clogging effects) for enhanced absorption. It is naturally high in squalene, a component in human skin sebum, and softens the skin and high in oleic acid which also increases its absorptive properties. Other low comedogenic (<2), liquid fats or oils may be substituted: avocado oil, hempseed oil, almond oil.

When sourcing the Menthol (CAS No. 89-78-1), care is required to ensure that the compound used is a white crystalline substance, naturally derived from mint oil or synthetically produced. It is an FDA approved compound, using topical applications for certain pain conditions. It is currently not approved as an ingredient for the treatment of neuropathy. Aromatic essential oils, with a high degree of similar heat/cool topical sensation, may be substituted: *eucalyptus* oil, clove oil, tea tree oil, pine oils, *cassia* oils, mint oils.

When sourcing the Camphor (CAS No. 76-22-2), care is required to ensure that the compound used is derived from the wood of the camphor laurel (*Cinnamomum camphora*), with a low comedogenic score (2). It is an FDA approved compound used in topical applications for certain pain conditions. It is currently not approved as an ingredient for treating neuropathy. Aromatic essential oils, with a high degree of heat/cool sensation, may be substituted: *eucalyptus* oil, clove oil, tea tree oil, pine oils, *cassia* oils, and mint oils.

When sourcing the Isopropyl myristate (CAS No. 110-27-0), care is required to ensure that the compound used is a compound that is a combination of isopropyl alcohol and myristic acid. Classified also as an emollient, it is soluble in this formulation and used for its high transdermal absorption. Other fatty-acid and alcohol esters that exhibit these properties include isopropyl palmitate, octyl palmitate, octyl isonanoate, and isocetylstearate.

When sourcing the Beeswax (CAS No. 8012-89-3), care is required to ensure that the compound used is a refined yellow, natural, pharmaceutical/cosmetic grade. A solid wax with a very low comedogenic rating (0-2). Yellow beeswax is unbleached and filtered. It is produced by the honeybee, genus Apis. Beeswax has a relatively low melting point of 62-64 C (144-147 F), which makes it suitable as an ingredient in a topical formulation, which will require a skin-melt temperature of approximately 32 C (90 F). Suitable substitutions to the preferred ingredient are: white beeswax, synthetic beeswax, and low comedogenic waxes, fats, and hydrogenated oils, which include but are not limited to lanolin, candelilla, carnauba, and ceresin.

When sourcing the Cannabidiol, Broad-Spectrum Cannabidiol (whole plant less the psychoactive component), care is required to ensure that the compound used includes other cannabinoids, terpenes flavonoids, and other compounds, and that it is derived from the plants of the genus *Cannabis*.

Cannabinoid alternatives to this ingredient are:
1) Full-Spectrum Cannabidiol (whole plant and contains the psychoactive component), it includes other cannabinoids, terpenes, flavonoids and other compounds.
2) Cannabidiol Isolate (CBD Isolate), which does not contain any other compounds of the plant.

Ointment product formula 1 amounts are listed by % of final mixture by weight. As used here, CBD=golden colored cannabidiol distillate.

| INGREDIENT | OPTIMAL PERCENT (by weight) | RANGE |
|---|---|---|
| MENTHOL | 16 | not to exceed 16% |
| CAMPHOR | 11 | not to exceed 11% |
| BEESWAX | 20 | Adjusted* +/– |
| ISOPROPYL MYRISTATE | 25 | Adjusted* +/– |
| OLIVE OIL | 27.444 | Adjusted* +/– |
| CBD (92% distillate) | 0.556 | Calculated as** |
| Total | 100.000 | |

The formulation is then heated to a minimum of 66 C (150 F), not to exceed 82 C (180 F). Cool the mixture until room temperature, and the resulting ointment is ready to use.

The resulting ointment is then adjusted * based on human skin temperature difference. The ointment may be affected by ambient surrounding temperature, and an ingredient to increase or decrease viscosity can be added to adjust the viscosity, depending on the form of application used, including but not limited to dermal patches, roll-ons, and sprays.

Calculated ** on the basis of a 92% cannabidiol (CBD) content of wax distillate to achieve 10 mg/CBD per dose, a dose being 10 mg CBD/2.5 mL (½ teaspoon) of the formula.

Adjustments are necessary due to the natural variation of the plants and resulting extraction. The range of cannabidiol (CBD) content in the distillate will vary in concentration from batch to batch.

An ointment having a range as low as 5 mg CBD/2.5 ml of formula has also been found to be effective.

Density of the formula is 0.90 g/mL at room temperature 20-25 C (68-77 F).

Analysis of the formulation shows that the formulation is anhydrous, and without the presence of water there, the ointment cannot support biological processes, therefore no preservatives are necessary. However, the ointment could be formulated with methyl and propyl parabens, benzoates or sorbates or other preservatives to improve stability. However, further analysis shows that the formulation has less than 10 CFUs/g (colony forming units), which is the minimal detection limit. This quantifies the lack of any bacteria, molds and yeasts in the formulation. In addition the pH of the formulation is less than 4.0, the mildly acidic environment also inhibits growth of anaerobic encapsulated pathogens (genus Clostridia) that could be present in the formulation.

However, the addition of a natural preservative such as "grapefruit seed", which is rich in essential oils and antioxidants such as tocopherols, ascorbic acid and chelating agents, would insure the long-term stability of the formulation. In addition, other natural preservatives and additives can provide additional benefits. The additional formulation additives include: Leucidal Liquid—which is derived from radishes fermented with kimchii bacteria and is ECOCERT approved, is a natural moisturizer and may add moisturizing benefits; Leucidal Liquid PT, which is derived from fermentation of *lactobacillus* and is commonly found in opaque lotions & creams; Leucidal Liquid SF, which is derived from *lactobacillus* ferment and is REACH compliant, salicylate-free and a strong additive against fungi growth compared to Leucidal Liquid; NataPres, which is a radish root ferment filtrate, with honeysuckle & aspen bark extracts and it is ECOCERT approved; Phytocide Elderberry OS, which is derived from elderberries and is REACH compliant and Phytocide Aspen Bark, which is rich in salicylates, low to no irritation potential, GMO free and a skin conditioning agent and is REACH compliant. The natural preservatives and additives can be incorporated into the formulation such that they comprise of 1-10 percent of the by weight of the overall formulation.

Natural preservatives can be selected from the group consisting of antioxidants, T-50 Vitamin E Oil, Rosemary Oil Extract, Anti-Microbials, Grapefruit Seed Extract and Germaben II.

The following are alternative ointment formulations.

Alternative Ointment product formula 2 amounts, are listed by % of final mixture by weight. As used here, CBD=golden colored cannabidiol distillate.

| INGREDIENT | OPTIMAL PERCENT (by weight) | RANGE |
|---|---|---|
| MENTHOL | 16 | not to exceed 16% |
| CAMPHOR | 11 | not to exceed 11% |
| BEESWAX | 20 | Adjusted* +/− |
| ISOPROPYL MYRISTATE | 20 | Adjusted* +/− |
| GLYCYRRIZAGLABRA | 5 | Adjusted* +/− |
| OLIVE OIL | 27.444 | Adjusted* +/− |
| CBD (92% distillate) | 0.556 | Calculated as** |
| Total | 100.000 | |

Alternative Ointment product formula 3 amounts, are listed by % of final mixture by weight. As used here, CBD=golden colored cannabidiol distillate.

| INGREDIENT | OPTIMAL PERCENT (by weight) | RANGE |
|---|---|---|
| MENTHOL | 16 | not to exceed 16% |
| CAMPHOR | 11 | not to exceed 11% |
| BEESWAX | 15 | Adjusted* +/− |
| ISOPROPYL MYRISTATE | 20 | Adjusted* +/− |
| LEUCIDAL LIQUID | 5 | Adjusted* +/− |
| OLIVE OIL | 27.444 | Adjusted* +/− |
| CBD (92% distillate) | 0.556 | Calculated as** |
| Total | 100.000 | |

Alternative Ointment product formula 4 amounts, are listed by % of final mixture by weight. As used here, CBD=golden colored cannabidiol distillate

| INGREDIENT | OPTIMAL PERCENT (by weight) | RANGE |
|---|---|---|
| MENTHOL | 16 | not to exceed 16% |
| CAMPHOR | 11 | not to exceed 11% |
| BEESWAX | 15 | Adjusted* +/− |
| ISOPROPYL MYRISTATE | 20 | Adjusted* +/− |
| GLYCYRRIZAGLABRA | 5 | Adjusted* +/− |
| GRAPESEED EXTRACT | 5 | Adjusted* +/− |
| OLIVE OIL | 27.444 | Adjusted* +/− |
| CBD (92% distillate) | 0.556 | Calculated as** |
| Total | 100.000 | |

Test Methodology:

Referring to FIG. 1 Absorption Analysis: The absorption amount into the epidermis and dermis of the formula versus a control (a name brand petrolatum/paraffin based topical pain relief ointment containing menthol and camphor), was tested and replicated. The skin substrate used was pig's ears (Sus domesticus), not previously frozen.

The testing used the pig ears to replicate human skin. Pig skin is very similar to human skin, and it has been used in pre-clinical studies and for drug testing to replicate human skin. Pig skin is structurally similar to human epidermal thickness and dermal/epidermal thickness ratio.

First, four pig ears were weighed to arrive at a tare weight. Then, an equivalent amount of ointment, 5.0 g, is applied to each ear. First and second ears had 5 g of the current over the counter petrolatum/paraffin based topical pain relief ointment applied and spread evenly in a 10×10 cm (4×4 square inch) area. The third and fourth ears had the ointment of the instant invention applied to them and spread evenly in a 10×10 cm (4×4 square inch) square. The ears were weighed to arrive at a final weight of ear and ointment value for each ear. Then, each ear was placed in a temperature-controlled environment set to a temperature of 32 degrees C. (90 degrees F.). This was done to approximate the similar skin temperature as living human skin. The ears were kept in the controlled environment for 30 minutes. The relative humidity was 40%. When the ears were removed from the controlled environment, any excess ointment was with a clean lint free absorbent cloth to remove unabsorbed ointment prior to weighing. The results for the current over-the-counter petrolatum/paraffin based topical pain relief ointment control average, was 14% absorption (0.7 grams absorbed) per ear.

The ears which had the ointment of the instant invention applied to them averaged 99% absorption (4.9 grams absorbed).

Figure 2:
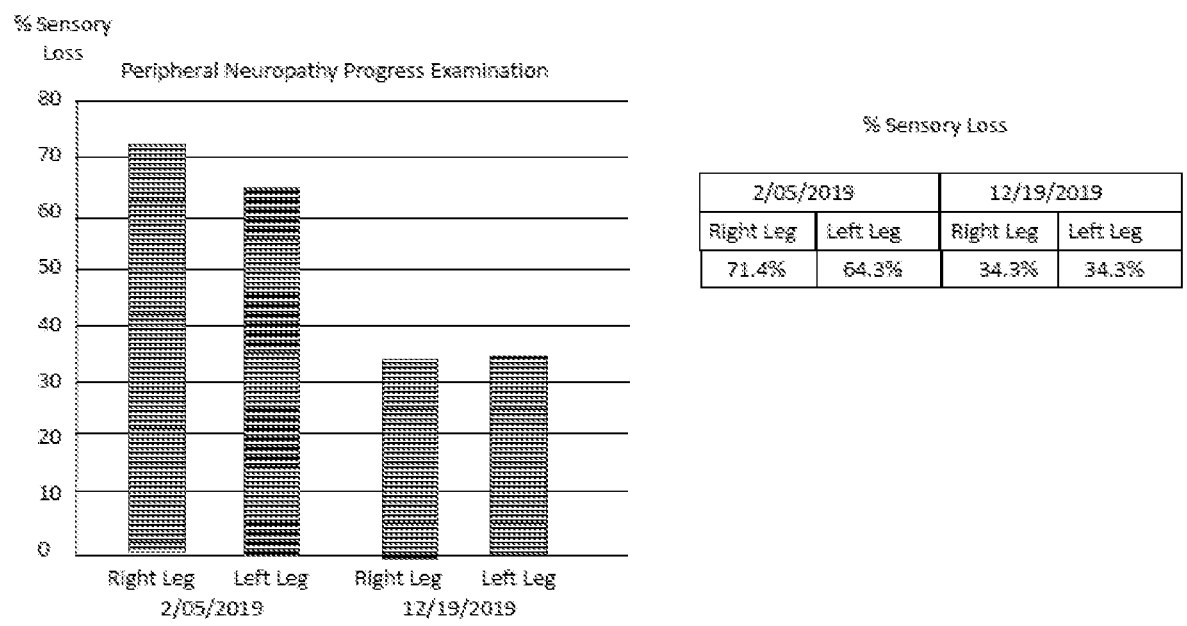
FIG. 2 shows a sample neuropathy assessment, showing before and after use of the instant invention.

Referring to FIG. 2 which provides efficacy results: a 58-year-old male subject, diagnosed with idiopathic polyneuropathy was treated with the formulation of the instant invention. No treatments had been successful in curing the condition or reducing symptoms.

The patient had experienced both feet that had numbness and occasional tingling and minor occasional pain increasing over the course of seven years. Baseline data evaluation showed a sensory loss of 71.4% in the right lower leg and a sensory loss of 64.3% in the left lower leg. After concluding a regimen use of the formula for a period of 4 months, along with certain lifestyle changes (reduced gluten intake, reduced alcohol consumption, diet modification resulting in a Body Mass Index (BMI) of 24 from 26) over a 10-month period, the results of the experiment was that the patient's right lower leg and lower left leg showed significant improvement with a sensory increase to a 34.3% loss in both limbs.

The examinations were administered independently, using the Toronto Clinical Scoring System/QST Exam of Lower Leg.

Figure 3:
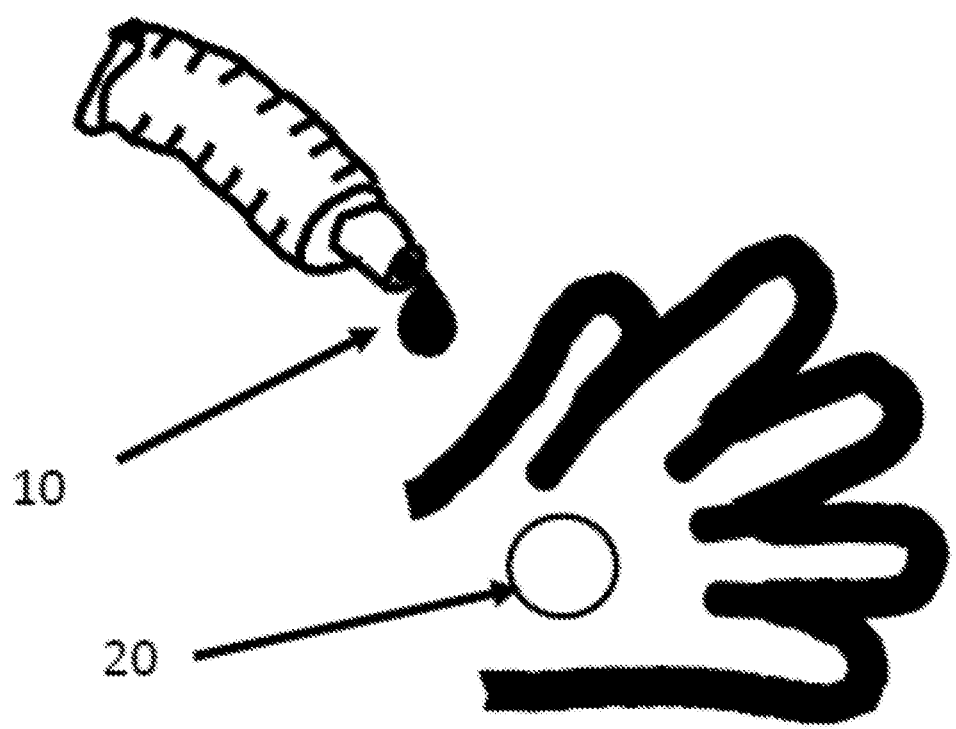
FIG. 3 shows the application of the topical transdermal pharmaceutical delivery system to the top of a hand.

Referring to FIG. 3, the cream or ointment 10 of the instant invention is applied to the target skin 20 and rubbed in until the ointment 10 is spread uniformly over the target skin area. This insures adequate coverage of the ointment 10 over the affected area.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains, and which fall within the limits of the appended claims.

What is claimed is:

1. A method of making a broad spectrum cannabidiol oil ointment consisting essentially of the steps of:
   a) harvesting cannabis;
   b) drying said harvested cannabis until the moisture content is approximately 5%;
   c) milling said dried cannabis into small pieces of a uniform size to form milled dried cannabis;
   d) visually inspecting and removing very large stems and any foreign material from said milled dried cannabis;
   e) cryogenically freezing said milled dried cannabis to −19° C. to form a cryogenically frozen milled dried cannabis;
   f) adding in pure ethanol and creating a ratio of 1:1 by weight of said ethanol to said cryogenically frozen milled dried cannabis and agitating it in a chilled jacketed kettle forming a hemp biomass;
   g) straining and centrifuging said hemp biomass;
   h) placing said strained and centrifuged hemp biomass from step g) into a suitable container and placing it under a high vacuum at 19° C. to form a dried material;
   i) winterizing said dried material by chilling to −40° C. and holding it at that temperature for 24 hours -36 hours which will form a winterized dried material;
   j) taking said winterized dried material and applying a vacuum through a buchner apparatus consisting essentially of a buchner funnel, a qualitative filter paper and a buchner flask, and then collecting the filtrate in the buchner flask;
   k) taking said filtrate and placing it in an oil bath at 121° C. to strip cannabidiol acid from the filtrate to form a decarboxylation biomass;
   l) taking said decarboxylation biomass and applying a high vacuum separating said decarboxylation biomass into plant material and golden colored cannabidiol oil distillate;
   m) taking said golden colored cannabidiol oil distillate, and placing it in a suitable container;
   n) taking said golden colored cannabidiol oil distillate, and adding in 0.556% by weight of the final mixture of said golden colored cannabidiol oil and placing it in a suitable glass beaker;
   o) adding in 27% by weight of the final mixture of the secondary active ingredients to said beaker;
   p) adding in 69.44% by weight carrier to said beaker;
   q) mixing and heating the contents of said beaker to a minimum of 66° C., not to exceed 82° C.;
   r) cooling the mixture to room temperature to form an ointment; and
   s) taking said ointment and placing it in a suitable container such as a jar or a tube.

* * * * *